(12) United States Patent
Jin et al.

(10) Patent No.: US 9,486,240 B2
(45) Date of Patent: Nov. 8, 2016

(54) INFLATABLE INSTRUMENT FOR TRANSANAL MINIMAL INVASIVE SURGERY

(71) Applicants: Heiying Jin, Nanjing (CN); Yifu Jin, Nanjing (CN)

(72) Inventors: Heiying Jin, Nanjing (CN); Yifu Jin, Nanjing (CN)

(73) Assignee: Heiying Jin

( * ) Notice: Subject to any disclaimer, the term of this patent is extended or adjusted under 35 U.S.C. 154(b) by 32 days.

(21) Appl. No.: 14/549,357

(22) Filed: Nov. 20, 2014

(65) Prior Publication Data

US 2016/0007985 A1  Jan. 14, 2016

(30) Foreign Application Priority Data

Jul. 8, 2014 (CN) .......................... 2014 1 0322755

(51) Int. Cl.
| | | |
|---|---|---|
| *A61B 17/02* | (2006.01) | |
| *A61B 17/34* | (2006.01) | |
| *A61B 19/00* | (2006.01) | |
| A61B 17/00 | (2006.01) | |

(52) U.S. Cl.
CPC ........... *A61B 17/3439* (2013.01); *A61B 17/02* (2013.01); *A61B 17/3421* (2013.01); *A61B 17/3423* (2013.01); *A61B 90/06* (2016.02); *A61B 2017/00557* (2013.01); *A61B 2017/0212* (2013.01); *A61B 2017/3452* (2013.01); *A61B 2090/065* (2016.02)

(58) Field of Classification Search
CPC .......... A61B 17/3423; A61B 17/0218; A61B 17/3421; A61B 17/3439; A61B 2017/00818; A61B 2017/0212; A61B 2017/3452; A61B 2017/00022; A61B 2017/0225
USPC ........................... 600/101–245; 606/108–207
See application file for complete search history.

(56) References Cited

U.S. PATENT DOCUMENTS

| | | | | |
|---|---|---|---|---|
| 6,616,603 | B1 * | 9/2003 | Fontana | A61B 1/31 600/170 |
| 8,894,572 | B2 * | 11/2014 | Bastia | A61B 17/0218 600/210 |
| 9,204,789 | B2 * | 12/2015 | Wenchell | A61B 1/00154 |
| 2007/0135803 | A1 * | 6/2007 | Belson | A61B 1/00154 606/1 |
| 2011/0112373 | A1 * | 5/2011 | Ainsworth | A61B 17/0218 600/207 |
| 2012/0095297 | A1 * | 4/2012 | Dang | A61B 17/0218 600/208 |

* cited by examiner

*Primary Examiner* — Pedro Philogene
(74) *Attorney, Agent, or Firm* — Treasure IP Group, LLC

(57) ABSTRACT

An inflatable assistive surgical instrument for transanal minimal invasive surgery, having a sheath that expands after inflation, is disclosed. The inflated sheath is cylindrical-shaped, and a notch is formed on the wall of the cylindrical sheath to expose the tissue of the colon wall for surgical operation. The inflatable sheath has an inflation nozzle for connecting with an inflating tube. The inflatable sheath disclosed in the present invention can fully achieve the expected effects and requirements and shows an extraordinary efficiency of the surgical operation, in comparison with the prior arts where the present invention is not adopted. The present invention also improves the quality and the success rate of surgical operation, and is highly appraised by the colorectal surgeons reduces the cost for single use.

18 Claims, 1 Drawing Sheet

INFLATABLE INSTRUMENT FOR TRANSANAL MINIMAL INVASIVE SURGERY

CROSS REFERENCE TO RELATED APPLICATION

This application claims priority to Chinese Application No. 201410322755.3, filed on Jul. 8, 2014. The Chinese Application is incorporated herein by reference in its entirety.

FIELD OF THE INVENTION

The present invention relates to an assistive surgical instrument for transanal minimal invasive surgery, and more particularly to a disposable assistive surgical instrument for transanal minimal invasive surgery.

BACKGROUND OF THE UTILITY MODEL

Transanal Endoscopic Microsurgery (TEM) is a surgical procedure that encompasses the endoscopic, laparoscopic and minimal invasive surgery techniques. The TEM technique was firstly described by Buess in Germany in 1984 and has been rapidly developed since then based on the continuous practices and innovation by colleagues of surgeons and the universal application of new techniques and instruments, and its surgical technique has become more mature. Hence, the TEM technique will become a first-choice surgical procedure of the partial colectomy for treatment of the rectal lesions particularly for those detected at the upper part which cannot be removed by using the traditional surgical instruments, and is also applicable for the partial colectomy of the middle and low rectal tumors which is hard to treat with the laparoscopic surgery. The TEM is performed under the transanal endoscopy for treatment of the early stage rectal cancer and removal of the benign rectal tumors, and for arresting hemorrhage and performing a series of delicate operations like stitching. The TEM featured in no skin incision, less trauma, accurate removal, quicker recovery, and accordingly has a wider prospect for application in the colon surgery.

Transanal Endoscopic Microsurgery (TEM) is an important approach for treatment of benign rectal tumors and early stage colon cancer, and the colo-anal anastomosis (Parks technique) is applicable for use in the sphincter-preserving surgery for low rectal cancer. The TEM is the most common practice of the transanal minimal invasive surgery and has been around for 20 years, but it is performed with use of the expensive surgery equipment (approximately ¥800,000), and the surgery equipment is not easy to manipulate and is difficult to change the angle of view, so the TEM is introduced in only a few hospitals. In recent years, a transanal minimal invasive surgery-TAMIS is introduced, which uses the single-incision laparoscopic surgical platform and does not require for special surgical equipment; however, this single-incision laparoscopic surgical platform needs insufflating gas, normally 12-15 mmHg, in colon so as to improve the view in the course of surgery, and the patient after surgery may experience bloating in the abdomen, and the peristalsis action of the colon makes it difficult to maintain the space for surgical operation.

Therefore, an assistive surgical instrument for transanal minimal invasive surgery, and more particularly a disposable assistive surgical instrument for transanal minimal invasive surgery is needed for solving the problems in the colorectal surgery field.

SUMMARY OF THE INVENTION

Accordingly, an objective of the present invention is to provide an assistive surgical instrument for transanal minimal invasive surgery, and more particularly a disposable assistive surgical instrument for transanal minimal invasive surgery.

According to a technical solution of the present invention, an inflatable assistive surgical instrument for transanal minimal invasive surgery is provided, which includes a sheath that expands after inflation. The inflated sheath is cylinder-shaped, and a notch is formed on the wall of the cylindrical sheath to expose the tissue of the colon wall for surgical operation. The inflatable sheath has an inflation nozzle for connecting with an inflating tube.

In addition, the sheath is closed on three sides and open on one side, forming a tunnel shape with a cross-section of U shape ($\Omega$ shape and so on). During the surgical operation, the open side is placed over the operation site (lesion site) on the tissue of the colon wall, and the three closed sides of the sheath are inflated to expand the colon canal to get a clear view during the surgical operation.

In addition, a surface pressure sensor is attached on the sheath cavity, and when a sheath inflating device is connected to inflate the sheath, a pressure display device displays the value of pressure to ensure that the pressure between the sheath and the colon wall is not too much to cause trauma of the colon wall.

In addition, a closing membrane is formed at a distal end (on the inner side) of the sheath to prevent the fecal matters in the colon moving down and blocking the field of view during operation. A plurality of protrusions (such as bars) is designed on the open side of the sheath, i.e., on the collar of the two sides of the U shape, for securing to the intestinal mucosa.

A proximal end i.e. anal end (outer side) of the sheath is connected with an elastic anal spreader (tube). The anal spreader is 5 cm long, and the end of the anal spreader is provided with a sealing disc with multiple holes, serving as an adapter (similar to the adapter for the laparoscopic surgical operation), the multiple holes are provided for inserting or withdrawing the surgical operation instruments and performing the operation.

A guiding stripe 6 is arranged along the length direction of the ridge of the U shape, and the guiding stripe includes a hard wire or a thickened rib or a thin tube (independent inflation or guide wire). The surgical operation instrument of the present invention is inserted to its full length into a human body via the anus prior to inflation, and then the instrument is inflated, which minimize the negative effects on the patient during this procedure.

The cross-section of the sheath is U-shaped, and the U shape of the distal end is the reinforced U-shaped rib, which facilitates expanding during the inflation. The cross-section of the U-shaped distal end of the sheath is smaller than the cross-section of the U-shaped proximal end of the sheath.

The present invention is a product made of an inflatable plastic material (or a polymer material such as latex or PU), which reduces the cost for single use, and eliminates the risk of cross-infection and provides the convenience for the doctors in use.

The present invention has the following efficacy. The assistive surgical instrument for transanal minimal invasive surgery, and more particularly the disposable assistive surgical instrument for transanal minimal invasive surgery disclosed in the present invention can guarantee the clear view of the surgical operation. The guiding stripe is arranged along the length direction of the ridge of the U shape includes a hard wire or a rib or a thin tube featured in the independent inflation. The surgical operation instrument of the present invention is inserted to its full length into a human body via the anus prior to inflation, and then the instrument is inflated and exposes the site for surgical operation. The present invention is adopted in practices in the facility where the applicant is employed, and according to the results, the present invention can fully achieve the expected effects and requirements and shows an extraordinary efficiency of the surgical operation in comparison with those where the present invention is not adopted. The present invention also improves the quality and the success rate of surgical operation, is highly appraised by the colorectal surgeons and reduces the cost for single use, thus reducing the financial burden of the patients. In terms of the surgical operation effects, the present invention can replace the surgical operation equipment used in the TEM.

DETAILED DESCRIPTION OF THE INVENTION

Figure 1:
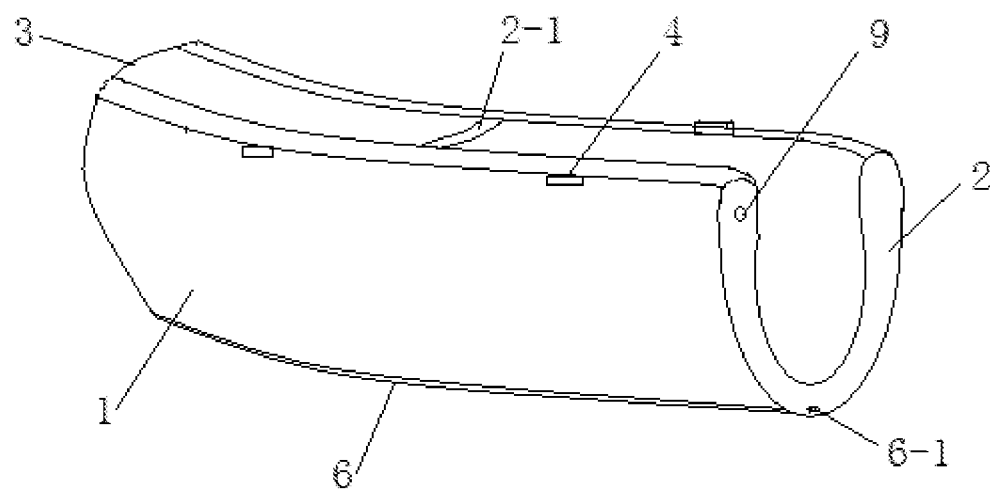
FIG. 1 is a schematic structural view of the inflatable sheath of the present invention after inflation.
Figure 2:
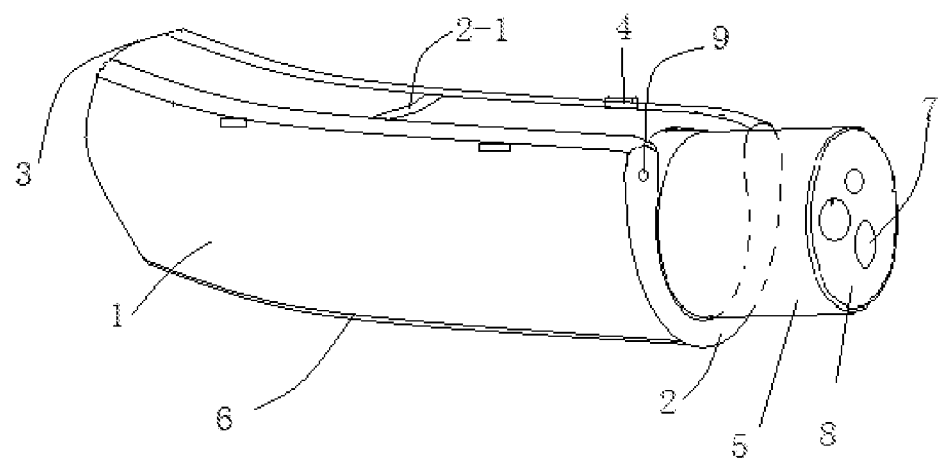
FIG. 2 is a schematic structural view of the present invention having a spreader tube and a porous sealing disc.

According to an embodiment of the present invention, a sheath 1 is provided, which includes an inflation nozzle 9 whose length is 10 cm or 18 cm or any other lengths, and the sheath is closed on three sides and open on one side, forming a tunnel shape 2 (with a cross-section of U shape). In preparation, a structure of a complete cylinder is first fabricated and then the cylindrical sheath is cut by means of thermal cutting to from the notch for surgical operation (for exposing the tissue for surgical operation after insertion) or a notch (alternatively e.g. the U shape cross-section having one or more connection collars 2-1 at the open side as shown in the figure or a hollow inflating tube). During the surgical operation, the open side (or the notch) is placed over the operation site or the lesion site, and after the three closed sides of the sheath are inflated, the U-shaped slot or cylinder expands the colon canal to get a clear view at the notch during the surgical operation. To reposition, deflate slightly and then adjust the position. A surface pressure sensor is attached on the three sides of the sheath, and a sheath inflating device is connected, so as to ensure that the pressure between the sheath and the colon wall is not too much to cause trauma of the colon wall. A closing membrane 3 is formed at a distal end of the sheath to prevent the fecal matters in the colon moving down and block the field of view during operation. A plurality of protrusions 4 is designed on the collar of the open side of the sheath, for securing to the intestinal mucosa. A proximal end i.e. anal end of the sheath is connected with an elastic anal spreader 5, the anal spreader is 5 cm long, and the collar can be stitched together for securing. The anal spreader 5 is connected to an adapter 8 having a sealing structure with multiple holes (similar to the adapter for the laparoscopic surgical operation), and the multiple holes 7 of the adapter 8 are provided for inserting or withdrawing the surgical operation instruments and performing the operation.

The membrane for preparing the sheath of the expending structure must meet the requirement for thickness, i.e. around 0.1 mm, and preferably the membrane can be expanded with the less thickness. The membrane is made of any polymer material such as PU, PVC, PE. The surgical operation instrument of the present invention is inserted into a human body via the anus prior to inflation. A guiding stripe 6 is arranged along the length direction of the ridge of the U shape, and the guiding stripe includes a hard wire or a thickened rib or a thin tube (the inflating thin tube may also serve as a catheter guide rod 6-1 in the figure). The surface of the sheath is wet with lubricant, and when reaching the position, the sheath is inflated to expand. After inflation, an anal spreader 5 is connected to the proximal end of the sheath, in which the anal spreader is a cylindrical (or slightly tapered) tube, and the outer end of the anal spreader is installed with an adapter 8 that has a sealing structure with multiple holes.

The pressure sensor is a semi-conductor chip structure, and can be withdrawn by a guide wire via the inflation nozzle, and a wireless pressure sensor may also be adopted, which has no negative effects on the patients.

The sheaths without the pressure sensor may also be adopted, whose diameters after inflation meet a series of specifications for a wide use in different fields or for different patients, thus having a wide application.

We claim:

1. An inflatable assistive surgical instrument for transanal minimal invasive surgery on a disease area, comprising
    a sheath that expands after inflation, wherein the inflated sheath is cylinder-shaped, and
    a notch, formed on a wall of the cylindrical sheath at any size and shape customized to expose the disease area on a colon wall for a surgical operation, and the inflatable sheath has an inflation nozzle for connecting with an inflating tube, and the sheath is configured to be inflated to expand a colon canal to get a clear view during the surgical operation;
    wherein
    a proximal end of the sheath is connected with an elastic anal spreader and the anal spreader is provided with a sealing disc with multiple holes, serving as an adapter;
    the sheath is made of any polymer material selected from PU, PVC, and PE, at a thickness of 0.1 mm or less, and a cross-section of the sheath formed after inflated at the diseases area can be a U-shape including a Ω shape;
    one or more connecting collars are disposed on the notch of the sheath securing to intestinal mucosa at the disease area.

2. The instrument according to claim 1 wherein the sheath is closed on three sides and open on one side, forming a tunnel shape having a U shaped cross-section.

3. The instrument according to claim 1, wherein a closing membrane is formed at a distal end (on the inner side) of the sheath to prevent the fecal matters in the colon moving down and block a field of view during the surgical operation.

4. The instrument according to claim 1, wherein a plurality of protrusions is disposed on the open side of the sheath.

5. The instrument according to claim 1, wherein a guiding stripe is arranged along a length direction of the ridge of the U shape, and the guiding stripe includes a hard wire or a thickened rib or a thin tube so that a surgical operation instrument can be inserted to its full length into a human body via the anus prior to inflation, and then the instrument is inflated.

6. The instrument according to claim 1, wherein the cross-section of the sheath is U-shaped, and the distal end of the U-shaped sheath is a reinforced U-shaped rib, which facilitates expanding during the inflation, and wherein the cross-section of the distal end of the U-shaped sheath is smaller than the cross-section of the proximal end of the U-shaped sheath.

7. The instrument according to claim 1, wherein a structure of a complete cylinder is first fabricated and then the cylindrical sheath is cut by means of thermal cutting to form the notch for the surgical operation.

8. The instrument according to claim 1, wherein a pressure sensor is attached on a sheath cavity, and as a sheath inflating device is connected to inflate the sheath, a pressure display device can display a value of pressure between the sheath and the colon wall.

9. The instrument according to claim 1, wherein the guiding stripe includes a hard wire or a thickened rib or a thin tube.

10. The instrument according to claim 2, wherein the open side is placed over an operation site during a surgical operation.

11. The instrument according to claim 2, wherein a closing membrane is formed at a distal end (on the inner side) of the sheath to prevent the fecal matters in the colon moving down and block a field of view during the surgical operation.

12. The instrument according to claim 3, wherein a plurality of protrusions is disposed on the open side of the sheath.

13. The instrument according to claim 3, wherein a proximal end of the sheath is connected with an elastic anal spreader and the anal spreader is provided with a sealing disc with multiple holes, serving as an adapter.

14. The instrument according to claim 3, wherein a guiding stripe is arranged along a length direction of the ridge of the U shape, and the guiding stripe includes a hard wire or a thickened rib or a thin tube, so that the surgical operation instrument can be inserted to its full length into a human body via the anus prior to inflation, and then the instrument is inflated.

15. The instrument according to claim 3, wherein the cross-section of the sheath is U-shaped, and the distal end of the U-shape sheath is a reinforced U-shaped rib, which facilitates expanding during the inflation, and wherein the cross-section of the distal end of the U-shaped sheath is smaller than the cross-section of the U-shaped proximal end of the U-shaped sheath.

16. The instrument according to claim 2, wherein a structure of a complete cylinder is first fabricated and then the cylindrical sheath is cut by means of thermal cutting to form from the notch for the surgical operation.

17. The instrument according to claim 2, wherein a pressure sensor is attached on a sheath cavity, and when as a sheath inflating device is connected to inflate the sheath, a pressure display device can display a value of pressure to ensure that the pressure between the sheath and the colon wall.

18. The instrument according to claim 2, wherein the guiding stripe includes a hard wire or a thickened rib or a thin tube.

* * * * *